United States Patent [19]

Thorpe et al.

[11] Patent Number: 4,824,792
[45] Date of Patent: Apr. 25, 1989

[54] APPARATUS AND A METHOD FOR REMOVING A SOLUTE FROM A SOLVENT

[75] Inventors: Michael Thorpe, Bristol; William J. Hoskin, Harpenden; Leslie Brown, Wern Tarw, all of United Kingdom

[73] Assignee: Analink Developments Limited, Cardiff, United Kingdom

[21] Appl. No.: 937,026

[22] Filed: Dec. 2, 1986

[30] Foreign Application Priority Data

Dec. 11, 1985 [GB] United Kingdom ............... 8530511

[51] Int. Cl.⁴ .................... G01N 1/18; G01N 1/22; G01N 25/22
[52] U.S. Cl. .................... 436/177; 436/178; 436/181; 436/175; 436/157; 436/158; 436/159; 422/66; 422/70; 422/80
[58] Field of Search .............. 436/157, 158, 159, 175, 436/177, 178, 181; 422/66, 70, 78, 80, 65

[56] References Cited

U.S. PATENT DOCUMENTS

| | | | |
|---|---|---|---|
| 3,954,408 | 5/1976 | Dugger | 436/159 X |
| 4,113,383 | 9/1978 | Burns et al. | 422/65 X |
| 4,133,640 | 1/1979 | Clinton et al. | 422/78 X |
| 4,552,723 | 11/1985 | Adams et al. | 422/66 |
| 4,647,431 | 3/1987 | Sekine et al. | 422/99 X |
| 4,740,298 | 4/1988 | Andresen et al. | 422/66 X |

FOREIGN PATENT DOCUMENTS 6902107 8/1970 Netherlands ............ 422/66

Primary Examiner—Barry S. Richman
Assistant Examiner—Lynn M. Kummert
Attorney, Agent, or Firm—Christie, Parker & Hale

[57] ABSTRACT

The apparatus includes an endless belt of nickel having a surface profile comprising an array of cavities such that any liquid layer deposited on the surface is keyed into the surface and constrained against movement relative to the surface. A liquid comprising solute and solvent is deposited as a layer on the belt from a nozzle. A first heater evaporates the solvent but leaves the solute. A second heater evaporates the solute which is then collected and fed to an analyzing device. The profile of the belt is particularly conducive to constraining a liquid on the belt and ensuring uniform evaporation upon heating.

12 Claims, 8 Drawing Sheets

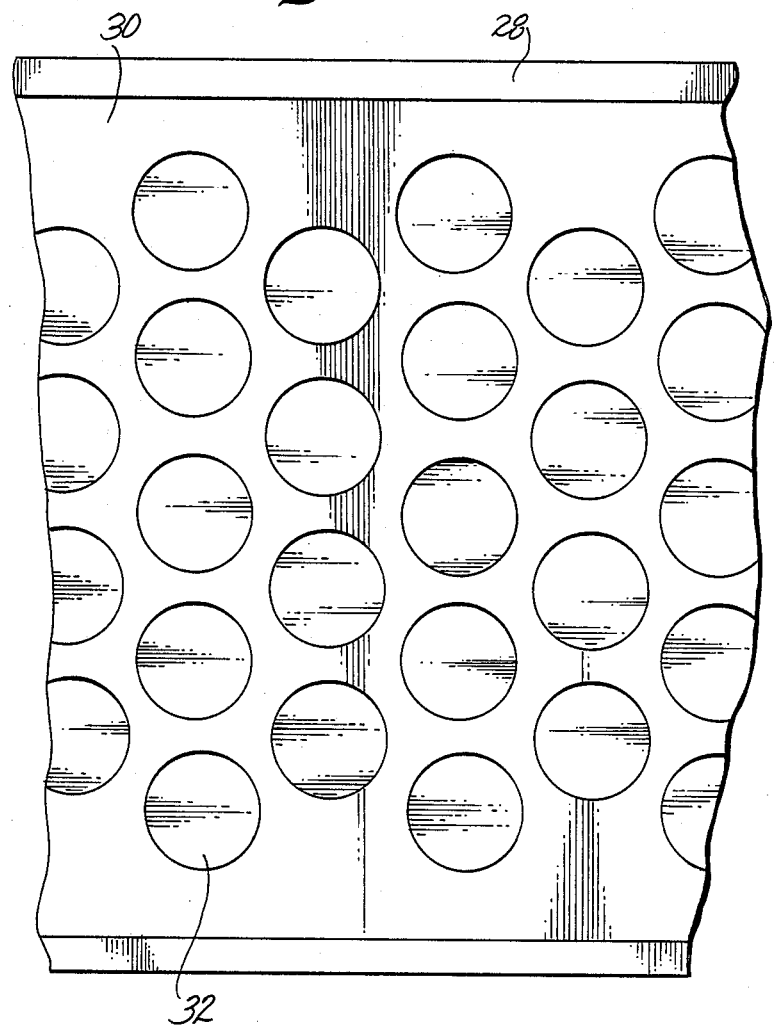

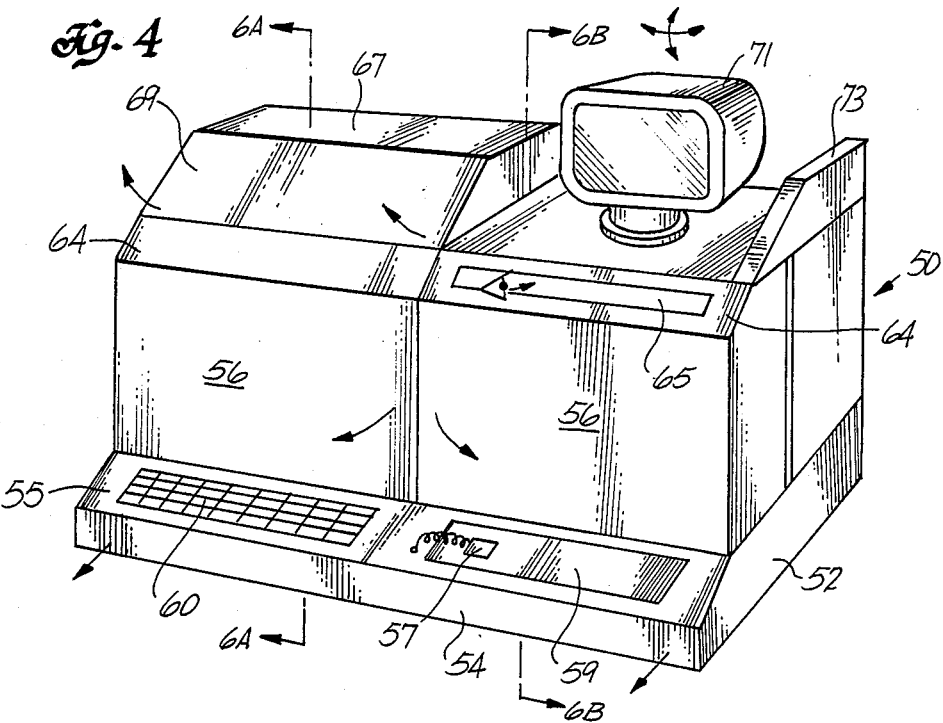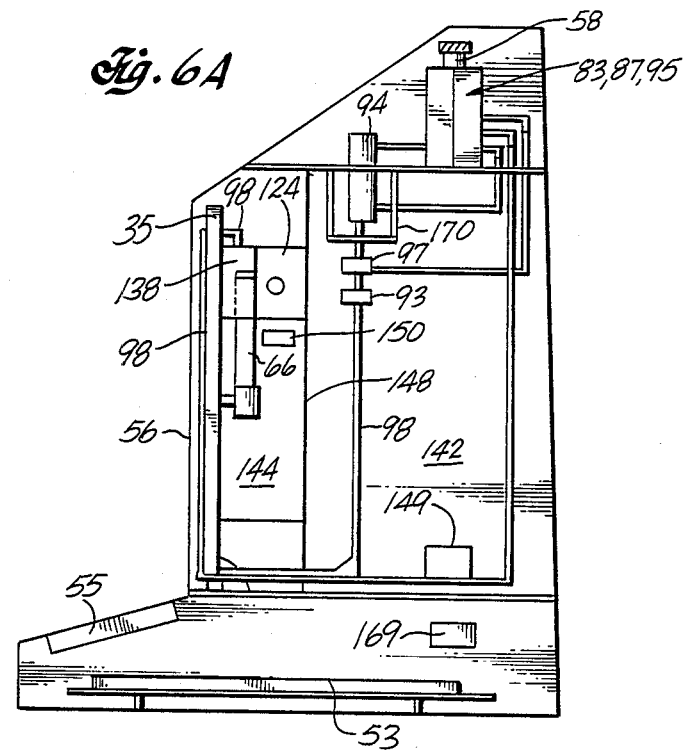

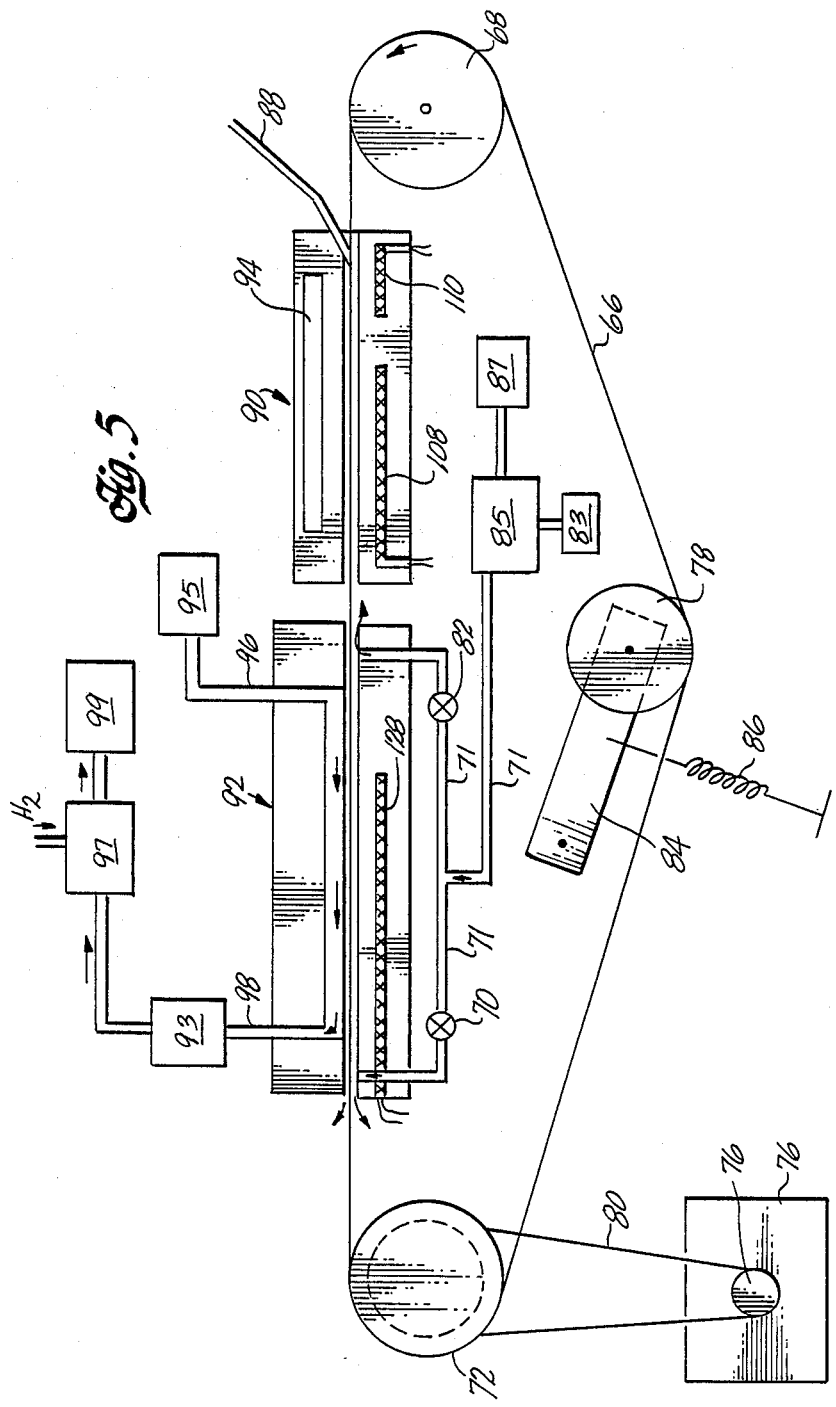

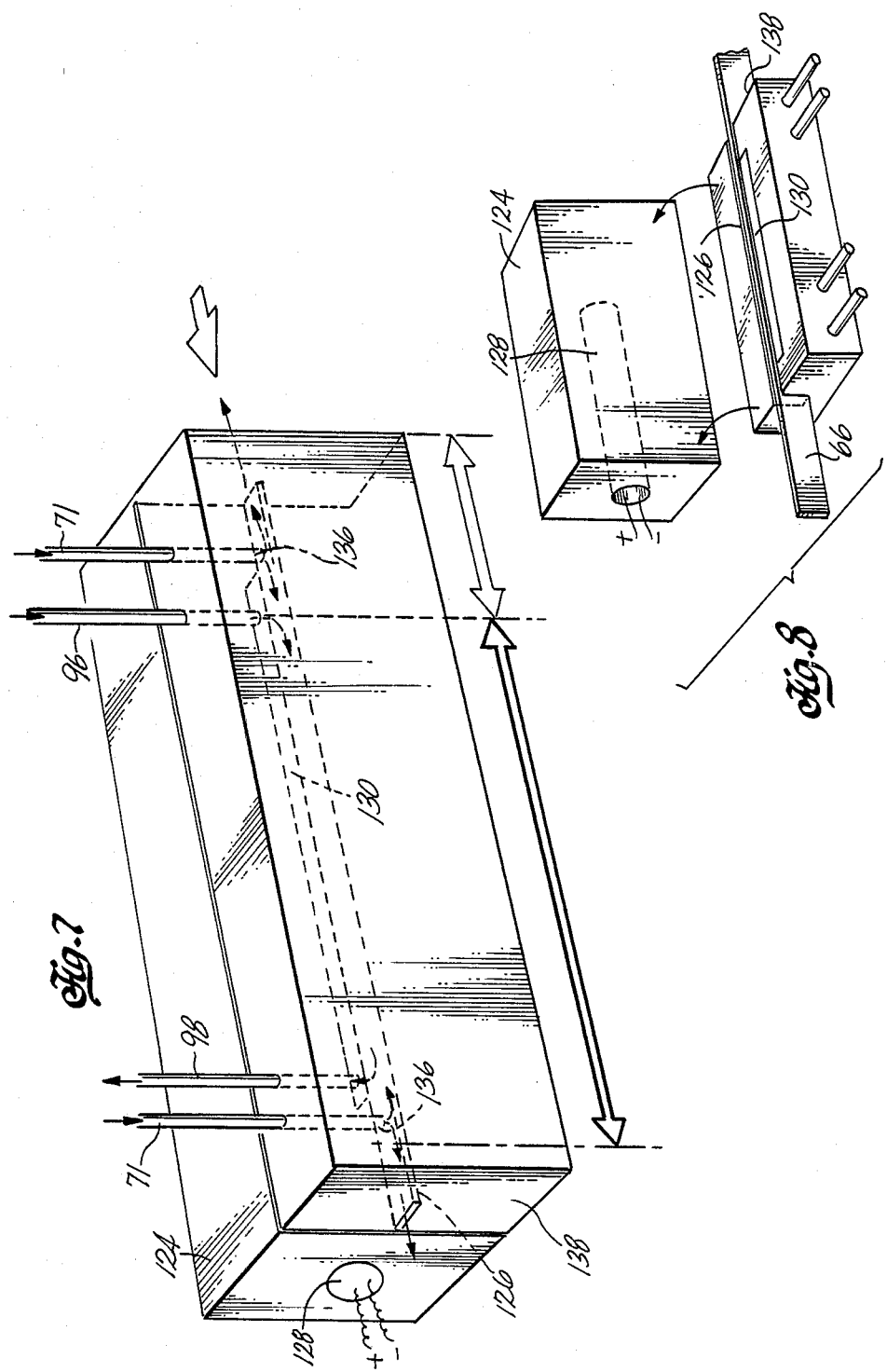

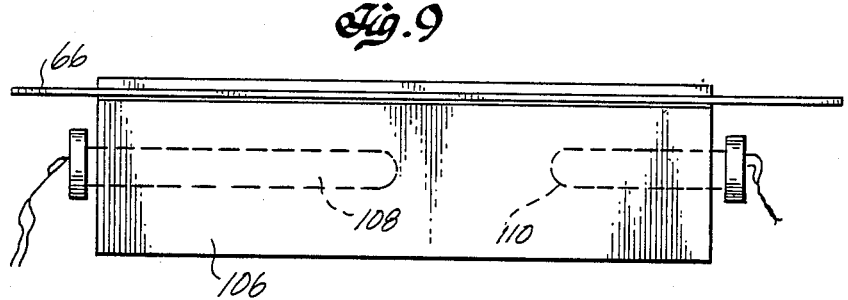
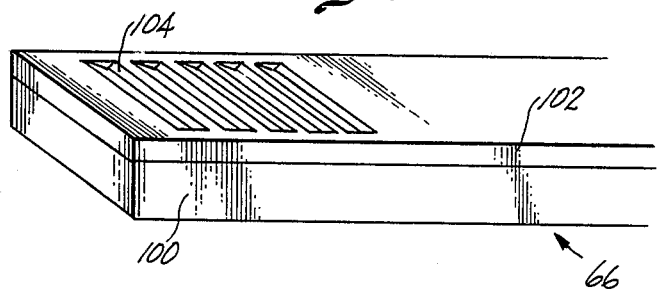

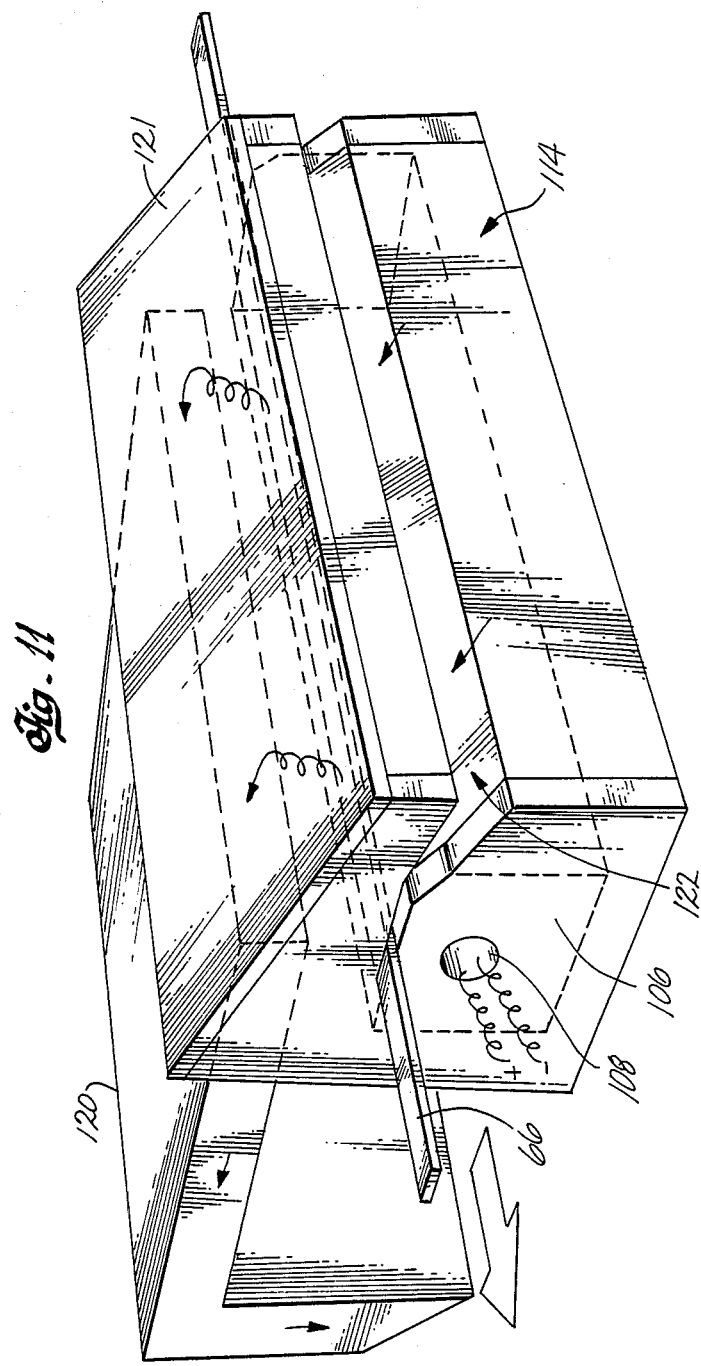

APPARATUS AND A METHOD FOR REMOVING A SOLUTE FROM A SOLVENT

BACKGROUND OF THE INVENTION

1. Field of the Invention

The present invention relates to an apparatus for and a method of processing a solvent containing a solute.

2. Description of the Prior Art

In liquid chromatography solute samples are dissolved in a liquid and injected into a flowing liquid steam of eluent or solvent to be chromatographed. The samples are spacially separated and are expelled from the chromatograph in discrete volumes. In the chromatograph the discrete solutes of each sample become physically separated in space and so separated in time when discharged from the chromatography. The different discrete solutes are collected as they emerge and are separately analysed.

In order to effect a proper analysis, all of the solvent must be removed from each collected volume. Since the solvent usually has a lower boiling point than the solute, this is done by heating the collected volume until all the solvent has evaporated. Thereafter the remaining solute is heated more severely and simultaneously reduced or oxidised to break down the sample component into a gas or gases which is or are then subjected to a gas analysis.

Where only small volumes of the sample are available, care must be taken to ensure the different solutes are collected separately and consequently no satisfactory automation of the process has yet been achieved.

It is an object of the invention to provide an improved method and apparatus for processing a solvent containing a solute.

SUMMARY OF THE INVENTION

According to the present invention there is provided apparatus for processing a solvent containing a solute comprising a conveyor belt for conveying a solvent containing a solute, the supporting surface of the belt being profiled to allow the solvent to key into the surface and so resist displacement forces acting to displace the solvent relative to the belt; means for dispensing a solvent containing solute on to the belt, a desolvator located against said belt for removing deposited solvent from the belt to leave the solute; and an oven located adjacent the belt downstream of the desolvator for converting the solute into gaseous form.

According to the present invention there is further provided apparatus for removing a solute from a solvent comprising a belt for carrying a layer of liquid comprising a solvent and a solute through a heating station, the belt having a surface profile comprises an array of cavities, each said cavity being of truncated part spherical configuration with the cross-section of the cavity increasing with distance from the opening thereof.

According to the present invention there is yet further provided a method of removing a solute from a solvent comprising the steps of providing a belt with a surface configuration such that when a layer of liquid is deposited thereon the liquid becomes keyed into the surface, depositing a layer of said liquid on said belt and displacing the belt through a first heating station having a temperature sufficient to cause the solvent to evaporate but to leave said solute on the belt.

BRIEF DESCRIPTION OF THE DRAWINGS

Apparatus for and a method of processing a solvent containing a solute will now be described, by way of example, with reference to the accompanying diagrammatic drawings, in which:

FIG. 2 is a fragmentary plan view (to an enlarged scale) of the liquid transfer belt of the apparatus;

FIG. 4 is a perspective view of the cabinet for another apparatus embodying the invention;

FIG. 5 is a front elevation of the general arrangement of the components of FIG. 4;

FIG. 6A is a cross-section through the cabinet of FIG. 4 along the line A—A;

FIG. 7 is a perspective view of the oven of the apparatus;

FIG. 8 is a perspective view to a reduced scale of the oven of FIG. 7 when in an opened state;

FIG. 9 is a side elevation of the desolvator of the apparatus of FIG. 5;

FIG. 10 is a perspective view of a fragment of the belt of the apparatus of FIG. 5; and FIG. 11 is a perspective view of a modified desolvator.

DESCRIPTION OF THE PREFERRED EMBODIMENTS

Figure 1:
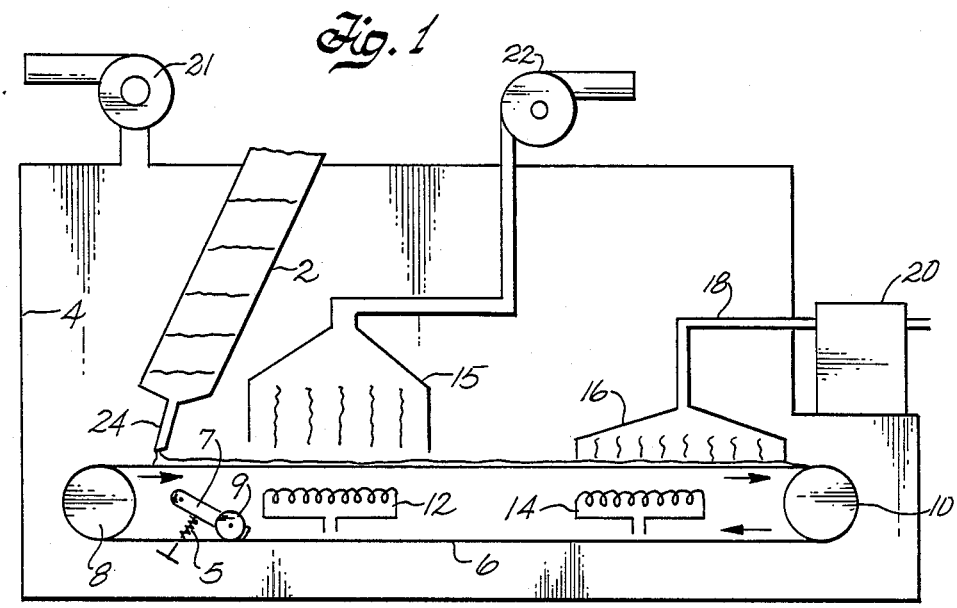
FIG. 1 is a front elevation of the apparatus.

As shown in FIG. 1, a liquid chromatograph 2 is partly housed in an enclosed chamber 4. Mounted in the chamber 4 is an endless belt 6 supported by a pair of rollers 8 and 10. A tension pulley 9 mounted on a pivoted lever 7 and biassed by a spring 5 acts to maintain the belt taut, in particular when it stretches due to heating. The chromatograph 2 has a discharge nozzle 24 which acts to discharge the contents as a liquid layer on to the upstream end of the upper run of the belt 6.

Below the upper run of the belt, in an intermediate section thereof, is a first electric heater 12. A collector system 15 is located above the heater 12 to collect evaporated solvent. Below the upper run of the belt at a downstream end portion thereof, is a second electric heater 14. A gas collector system 16 is located above the downstream end of the upper run of the belt. The collector system 16 is coupled by a tube 18 to a gas analysis instrument 20 which may for example analyze the gas sample spectrographically.

An extractor fan 22 is coupled to the collector system 15 to extract evaporated solvent to prevent it from entering the chamber and to dispose of it in a region outside the building in which the measurements are being made.

In operation, the liquid is dispensed from the nozzle 24 and deposited on the belt 6 which conveys the resulting liquid layer to a first heating station defined by the heater 12. The heat provided is sufficient to evaporate all of the solvent from the solute. The evaporated solvent is extracted ensuring no contamination in the chamber 4 by means of the air extractor fan 22. The solute which remains on the belt then passes to a second heating station defined by the heater 14.

Here the temperature is higher than in the first heating station and so the solute is reduced or oxidised and converted into a gaseous form. The resultant gases are collected by the collector system 16 and fed to the instrument 20 for analysis. The movement of the evaporated solute along the tube 18 can be assisted by a fan (not shown) or means providing a vacuum or a venturi suction. A cooling fan 21 supplies a flow of cool air to the chamber 4.

In order to ensure uniform evaporation of the liquid, at the first station, and to prevent the liquid from running freely over the surface of the belt 6, the surface of the belt 6 is specially profiled.

Figure 3:
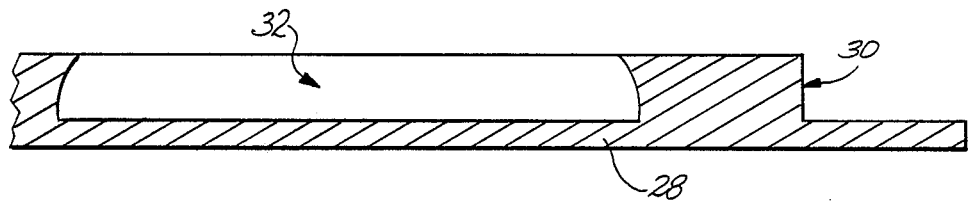
FIG. 3 is a section to a yet further enlarged scale of the belt of FIG. 2.

As shown in FIG. 2, the belt 6, which is substantially pure nickel and therefore has catalytic properties, has a laminar base portion 28 supporting a raised central portion 30 in which there are an array of cavities 32. Each cavity 32 is of circular cross-section and reduces in diameter with distance from the base portion 28 (see FIG. 3). The sides of each cavity are preferably concave.

The cavities are preferably arranged in rows and columns with each alternate column being displaced by half one pitch in the direction of the column relative to the cavities in the intervening columns; one pitch being the distance between the centres of adjacent cavities in the same column.

The belt 6 is typically $7\pm0.6$ mm wide and has a maximum thickness of 0.50 mm. Each cavity is 1 mm in diameter at its mouth and increases in diameter with depth.

The tangents to adjacent columns of cavities are spaced some 0.09 mm apart while the centres of adjacent cavities in the same column are separated by 1.26 mm.

The purpose of the cavities is to retain the layer of liquid on the belt while the belt is being displaced and for this purpose the density of cavities, their size ranges and their profiles are of significance.

Preferably there are from 4 to 0.05 cavities per $mm^2$. The cavities should have openings ranging from 6 to 0.15 mm in diameter and should be of truncated part spherical configuration so that as viewed from the side each cavity has an overhanging edge. Instead of being circular the cavities can be square, hexagonal or of other multisided configuration.

Typically the depth of each cavity is 0.12 mm but the depth can vary from 0.01 to 0.45 mm.

Advantageously the ratio of width to depth of cavity varies in the range of from 4:1 to 16:1.

In a modification instead of cavities, meandering valleys can be provided in the raised portion, with the cliff wall of each valley being sufficient to constrain a layer of liquid deposited on said surface from movement relative to the belt.

In effect the provision of the cliff wall acts to key in the layer of liquid to the surface.

With the surface pock-marked with an array of cavities as described, it has been found that the heat imparted to the layer of liquid carried by the belt, through the material of the belt, ensures a uniform evaporation of the solvent from the layer and therefore a homogeneous residue for conversion to a gaseous form at the second heating station.

The apparatus shown in FIGS. 4 to 10 includes a cabinet 50 (see FIG. 4) having a plinth 52 which houses a drawer 54 containing electronic circuitry 53 (e.g. circuit boards). The drawer 54 can be pulled open from the front of the cabinet 50 to expose the electronic circuitry 53. A projecting front portion of the drawer 54 has a sloping panel carrying a keyboard 60, a "mouse" 57 and pad 59.

Mounted on the front face of the cabinet are a pair of doors 56 which are hinged along their side edges. A seal (not shown) is provided between the door and the body of the cabinet to provide an air tight seal to prevent the escape of gases from the cabinet. A sloping panel 64 above one of the doors 56 has a viewing window 65.

Magnetic or other types of catch can be used to hold the doors 56 closed. The body of the cabinet carries a housing 67 having a hinged perspex cover for providing access to a gas control unit 58 for controlling the flow of various gases (e.g. hydrogen, oxygen, air and helium/nitrogen/argon) to the apparatus. A visual display unit 71 and a top module 73 are mounted on top of the cabinet 50 adjacent the housing 67 to display data pertinent to the operation of the apparatus. A chromatographic column (not shown) is supported on the side face of the cabinet and separates the solutes dissolved n a solvent. The solvent containing the solute is supplied to the column through a valve (not shown) at the lower end of the column. A pump (not shown) pumps the liquid through the chromatograph to a dispensing tube 88 within the apparatus.

As shown in FIG. 5 two rollers 68 and 72 define an upper run for an endless belt 66. A tension roller 78 bears against the lower run of the belt to tension the belt 66. The tension roller 78 is mounted at the free end of a pivoted arm 84 which is biassed about its pivotal point in a clockwise sense by gravity and if required by a spring 86.

A motor 76 has a drive pulley 74 which is coupled to the roller 72 by a drive belt 80.

The endless carrier belt 66, the rollers 68 and 72, the drive roller 80, the motor 76 and the tension roller 78 are all supported on the inner face of a cassette plate 35 hinged along its lower edge. When the doors 56 are open the cassette plate 35 is exposed and can be lowered to provide ready access to the belt and rollers for replacement or servicing. Raising of the cassette plate 35 brings the belt 66 back into cooperation with the remainder of the apparatus.

When the drive motor 76 is energised, the upper run of the belt 66 (which moves from right to left as viewed in FIG. 5) passes under a dispensing tube 88 through a desolvator 90 and then through an oven 92. The desolvator is provided with a housing coupled to a duct 94 through which evaporated solvent is discharged. The oven 92 has an inlet 96 which is supplied with a carrier gas from a source 95 and which carries the solute upon conversion to a gaseous form by the heat of the oven, to an outlet 98. The outlet 98 is coupled to a suction unit 93 which feeds the gases through a reduction unit 97 to a gas analyser 99. The reduction unit contains a catalyst and is supplied with hydrogen gas which enables the gases from the oven to be reduced. A ballast gas from a source 87 is suppled through ducts 71 to the oven to form a gas curtain around the area through which the carrier gas passes. Restrictors 70 and 82 enable the ballast gas pressure to be controlled and a mixing unit 85 enables a dopant from a gas source 83 to be introduced into the ballast gas.

The belt 66 preferably has catalytic properties to assist the break-up of the solute when heated into compounds in gaseous form. The belt 66 advantageously has a nickel content and can be for example of pure nickel, or a nickel stainless steel such as that known as INCONEL (Registered Trade Mark). Instead a nickel intermediate alloy, or a nickel solid solution alloy or any other material which catalyses the oxidative or reductive pyrolysis of organic compounds can be used.

The upper run of the upper surface of the belt must also be specially profiled to prevent deposited solvent (containing a solute) from running freely over the surface.

When solvent deposited on a belt, approaches a source of heat there is a tendency for the solvent on the belt to move in the reverse direction.

The surface of the belt must therefore be provided with barriers or walls which resist movement both longitudinally and laterally of the belt. One profile for the belt surface has already been described in conjunction with FIGS. 2 and 3. Another profile is shown in FIG. 10. In FIG. 10 the belt comprises a substrate 100 carrying a layer which has been selectively electroformed or etched to define a series of V- or U-shaped grooves 104 extending at right angles to the longitudinal axis of the belt 66. Other profiles which can retain a thin deposit of solvent (containing solute) and at the same time resist its migration in the horizontal plane can also be adopted.

In order that a sufficiently thin layer of solvent (containing solute) be deposited on the belt through the dispensing tube 88 it is important to break up surface tension forces and so the lower end of the tube should be placed as close to the upper surface of the belt as possible. The spacing between the lower end of the tube and the upper surface of the belt should be less than that which would allow an individual droplet to form, but sufficient to allow the steady flow from the tube to the belt 66.

Also the lower end of the tube 88 should be located just inside the desolvator 90 so that any vaporized solvent cannot escape from the desolvator 90 other than through the duct 94. The heat generated by the desolvator 90 is used to preheat or partially vaporized the liquid in tube 88. Advantageously, a ballast gas may be fed through the tube to prevent the deposit of solute in the tube and/or to assist the flow of liquid on to the tape. By depositing solvent (containing solute) on a warm part of the belt 66 the solvent will more readily be evenly distributed as the surface tension is lowered as the temperature increases.

The desolvator 90 shown in FIG. 9 comprises an elongate heating block 106 which supports the belt on its upper surface.

The block 106 which may be of any suitable metal has a bore at its upstream end, housing a low power heater 110 and a bore at its downstream end housing a high power heater 108.

The low power heater 110 generates heat to slowly raise the temperature of the belt 66 as it enters the desolvator but not sufficient to cause deposited liquid to "spit". The high power heater 108 is arranged to heat the solvent to a temperature sufficiently high to remove all the solvent for a given solvent flow rate and a given tape speed, but in any event the solute should not be heated above a temperature which would convert it into gaseous form given the environmental conditions in the desolvator. Thus for example where the solvent is water the part of the heating block 106 in the region of the heater 108 is advantageously at a temperature of between 150° to 400° C.

A modified desolvator is shown in more detail in FIG. 11. As shown the block 106 is enclosed in a generally rectangular housing 114 having a transparent sloping lid 121. An upwardly inclined longitudinal extending slot 122 allows the belt to be inserted into the housing to rest on the block 106, when the cassette plate 35 is raised from the lowered position and into the upright position. The slot becomes progressively narrower with distance from the front of the housing to reduce the amount of air drawn into the housing 114 when the desolvator is operational. The rear face of the housing 114 communicates with an exhaust manifold 120 coupled to an extraction unit. The lid 121 is for example of PYREX (RTM). In operation a vacuum is applied to the manifold 120 when the belt 66 is driven through the housing 114. As the solvent evaporates the evaporated solvent is drawn into the manifold 120.

The creation of a partial vacuum in the chamber pulls the ambient air in the cabinet through the slot and so prevents the escape of solvent other than through the manifold, thus preventing the pollution of the immediately surrounding environment.

The combustion oven 92 is more clearly shown in FIGS. 7 and 8. The oven is divided into a stationary rear section defined by a longitudinally extending heating block 124 and a movable front section defined by heat conductive block 138 mounted on the cassette plate 35. When the cassette plate 35 is moved from the open and horizontal position to the upright position, the block 138 moves from the position shown in FIG. 8 to the position shown in FIG. 7 where it contacts the heating block 124 to conduct heat from the block 124 to the tape 66. The heat conductive block 138 has a lateral longitudinally extending slot 126 which accommodates the belt 66. A longitudinally extending bore in the downstream end of the heating block 124 accommodates a heater 128 which extends some three quarters of the length of the block from the downstream end of the block. The two blocks 124 and 138 when matingly engaged define four walls surrounding the belt. In the upper wall of the slot 126 directly above the belt lies a channel 130 which extends over a central length of the belt within the oven 92. The inlet 96, coupled to the channel 130 at the upstream end of the channel 130, supplies the channel with an inert carrier gas for example helium (argon or nitrogen can also be used). The carrier gas carries any gases generated, by the heating of the solute in the oven, along the channel 130 to the outlet 98.

Gas emerging from the outlet 98 is sucked into a gas analysis machine where the gas is analysed. Labyrinth ducts 136 are provided around channel 130 to provide a gas curtain around the channel 130 to prevent the escape of gas from the channel 130. The ducts 136 are supplied through the inlet 71 with a ballast gas, preferably having a similar composition to the carrier gas and this ballast gas escapes to the atmosphere. The object of the labyrinth ducts 136 is to surround the belt 66 and channel 130 with a wall of ballast gas to prevent the products of the heated solute escaping and to prevent the ingress of any air from the environment into the channel 136. In a modification the duct 136 may encircle the channel 130 two or more times.

The carrier gas is doped with 0.01 to 99% by weight of hydrogen or 0.01 to 99% by weight of oxygen to promote reduction or oxidation of the solute when heated. The ballast gas normally contains no such dopants. In a modification, however, the carrier gas inlet 96 may be omitted and the ballast gas is then drawn into the channel 130 by suction to take over the function of the carrier gas. In this event the ballast gas may be doped from the dopant source 83 (see FIG. 5). The ballast gas at the upstream end of the oven is not only directed in the direction in which the belt 66 is displaced but also along the surface of the belt in the upstream direction. Thus the ballast gas flowing over the belt 66 as it enters the block acts to cool the belt 66 so as to prevent the solute being prematurely converted into gases before the belt reaches the point at which it lies directly below the channel 130.

In a modification the block 124 may be reduced in cross-section at a position where the heater element ends to provide a thermal barrier. It will be seen that the oven is heated only over three quarters of its length (see the solid double headed arrow).

Figure 6B:
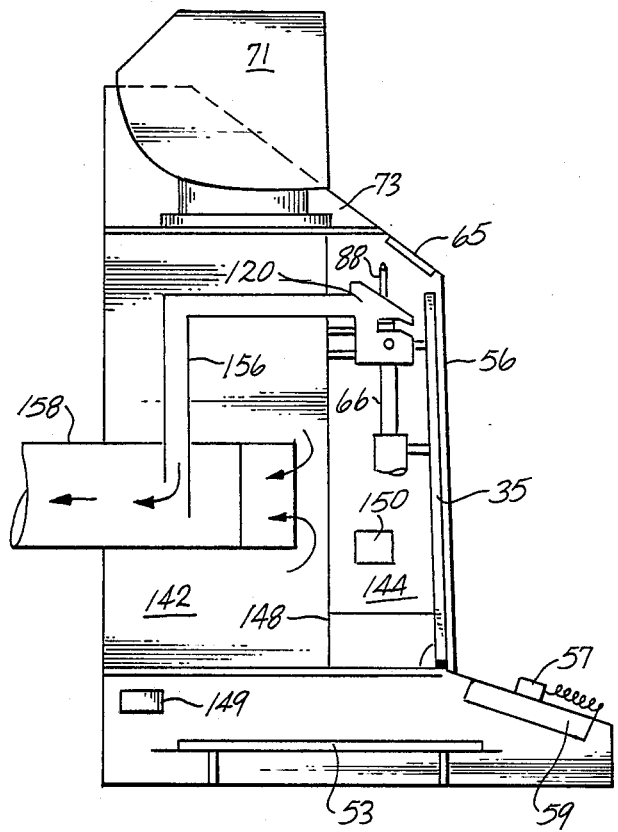
FIG. 6B is a cross-section through the cabinet of FIG. 4 along the line B—B.

The arrangement of the various components of the apparatus within the cabinet 50 is more clearly shown in FIGS. 6A and 6B.

As can be seen the cabinet is divided into two sealed chambers by a wall 148. One chamber 144 lies between the wall 148 and the doors 56 and the other chamber 142 lies on the opposite side of the wall 148 to the doors 56.

As previously mentioned a hinged cassette plate 35 supports all the pulleys, the front section 148 of the combustion oven 92 and the belt 66, while the dispensing tube 88, the desolvator 90, and the rear section 124 of the oven 92 are supported by the wall 148. Thus when the doors 56 are swung open and the cassette plate 35 is swung down, the belt 66 is neatly withdrawn from the dispensing tube 88, the desolvator 90 and the rear section 124 of the oven 92 so that it can be inspected, overhauled or replaced.

The chamber 144 houses fans 150 which draw air in from the environment and over the tape 66 where it is exposed to cool the tape 66 after it comes out of the oven and before it enters the oven. The chamber 142 is connected by an opening in an upper portion of the wall 148 to draw air from the chamber 144 and discharge it to a safe location preferably outside the building in which the apparatus is housed. This circulation of air has a cooling effect on the apparatus and collects and discharges excess ballast gases lost from the slot 126. A further duct 156 couples the exhaust manifold 120 into the duct 158 and draws the evaporated solvent by venturi action from the desolvator for subsequent safe discharge. Various other circulating and cooling fans 149 are provided.

As shown in FIG. 6A in particular the output duct 98 feeds the gaseous solute to suction unit 93 and then to the reducing unit 97. The reduced gases are then fed to the analyser 99 which is heated by another oven 170. The gas control unit 58 controls the supply of the gases from the sources 83, 87 and 95 to the different parts of the apparatus.

The belt is advantageously arranged to be driven at speeds in the range of from 4 to 400 cm/minute. At such speeds the desolvator should have sufficient length (from 4 to 40 cm) and be supplied with sufficient heat to evaporate at least 0.01 ml/minute of solvent.

The oven 92 should preferably be capable of being heated to temperatures in the range of from 700° to 900° C. and should be in excess of 4 cm in length.

The belt 66 is advantageously at least 20 cms in length and is capable of withstanding temperatures in excess of 500° C. Also it will be appreciated that while the displacement of the belt is normally continuous and at a constant speed it can be displaced in discrete steps.

While a presently preferred embodiment of the present invention has been illustrated and described, modificiations and variations thereof will be apparent to those skilled in the art given the teachings herein, and it is intended that all such modificiations and variations be encompassed within the scope of the appended claims.

We claim:

1. Apparatus for processing a solvent containing a solute comprising a conveyor belt for receiving a solvent containing a solute, the conveyor belt having a supporting surface defining a keying profile to allow the solvent to key into the surface and so resist displacement forces acting to displace the solvent relative to the belt at least in the direction of displacement of the belt;

means for dispensing a solvent containing solute onto the belt, a desolvator located against said belt for removing deposited solvent from the belt to leave the solute;

an oven located adjacent the belt downstream of the desolvator for converting the solute into gaseous form, and means for displacing the conveyor belt to carry the solute through the desolvator and into the oven.

2. Apparatus according to claim 1 wherein said belt is of catalytic material.

3. Apparatus according to claim 1 wherein said oven comprises heating means, a guide for guiding the belt into heat transfer relationship with the heating means, and means supplying a carrier gas to said supporting surface of the belt carrying the solute to entrain and carry away for analysis the gases produced as a result of heating the solute.

4. Apparatus according to claim 3 wherein said oven further comprises ballast gas supply means, and means for directing the ballast gas to create a wall of ballast gas around the carrier gas where it contacts the surface of the belt to constrain the carrier gas and the entrained gases against escape and to inhibit the contamination of the carrier gas by gases located outside the wall of ballast gas.

5. Apparatus according to claim 4 including means for directing a ballast gas from the oven and along the belt in a direction upstream of the oven to reduce the conduction of heat along the belt from the oven in the upstream direction and so inhibit premature gasification of the solute.

6. Apparatus according to claim 1 wherein the desolvator comprises a heating block, and means for heating the heating block to have a temperature gradient which increases in the downstream direction from a temperature insufficient to cause the solvent to spit, to a temperature in excess of that required to evaporate the solvent.

7. Apparatus according to claim 6 wherein the desolvator defines an enclosed chamber through which the belt runs and includes withdrawing means for withdrawing gas from said chamber at a rate sufficient to prevent the escape of gaseous solvent from the chamber other than through the withdrawing means.

8. Apparatus according to any preceding claim wherein the conveyor belt comprises an endless belt supported on rollers, and drive means for driving the belt.

9. Apparatus according to claim 8 wherein said oven is defined by two mating parts and including means defining a normally sealed chamber having a first wall supporting said desolvator and one of a pair of mating parts of said oven and a second wall facing the first wall and supporting the other of the mating part of the oven, the conveyor belt and the rollers, one of said walls being movable relative to the other wall to bring the conveyor belt into and out of cooperation with the desolvator and the said one part of the oven.

10. Apparatus for processing a solvent containing a solute comprising:

a conveyor belt having a carrier surface so profiled as to enable the solvent containing a solute to be generally uniformly disposed and keyed into the surface, and so resist displacement relative to the belt by forces acting on the solvent in the downstream direction of the belt, means for depositing the solvent containing the solute on the belt at an upstream location, and means for processing the solvent containing the solute, at a downstream station to remove the solvent and to convert the solute into a gaseous form.

11. Apparatus according to claim 10 wherein the belt has a surface profile comprising a raised area defining a plurality of recesses, walls defining said recesses having a liquid retaining profile for constraining liquid against movement relative to the belt.

12. Apparatus according to claim 10 wherein the belt has a surface profile comprising an array of cavities.

* * * * *

UNITED STATES PATENT AND TRADEMARK OFFICE
CERTIFICATE OF CORRECTION

PATENT NO. : 4,824,792
DATED : April 25, 1989
INVENTOR(S) : Michael Thorpe et al It is certified that error appears in the above-identified patent and that said Letters Patent is hereby corrected as shown below:

In the Specification:

Column 1, Line 18      Change "chromatography" to
                       -- chromatograph --

Column 2, Line 54      After "chamber" insert
                       -- 4 --

Column 4, Line 19      Change "n" to
                       -- in --

Column 5, Line 37      Change "vaporized" to
                       -- vaporize --

Signed and Sealed this

Twenty-eighth Day of August, 1990

Attest:

HARRY F. MANBECK, JR.

*Attesting Officer*          *Commissioner of Patents and Trademarks*